(12) United States Patent  (10) Patent No.: US 8,562,644 B2
Yuan et al.  (45) Date of Patent: Oct. 22, 2013

(54) BARBED SUTURE WITH NON-SYMMETRIC BARBS

(75) Inventors: Jie Jenny Yuan, Branchburg, NJ (US); John S. Crombie, East Hanover, NJ (US)

(73) Assignee: Ethicon, Inc., Somerville, NJ (US)

( * ) Notice: Subject to any disclaimer, the term of this patent is extended or adjusted under 35 U.S.C. 154(b) by 1070 days.

(21) Appl. No.: 11/834,033

(22) Filed: Aug. 6, 2007

(65) Prior Publication Data

US 2009/0043336 A1 Feb. 12, 2009

(51) Int. Cl.
*A61B 17/04* (2006.01)

(52) U.S. Cl.
USPC ....................................................... 606/228

(58) Field of Classification Search
USPC ........ 606/228–231; 57/200–260; 264/177.13, 264/172.11–172.18; 442/181–202; 15/207.2; 428/357–407
See application file for complete search history.

(56) References Cited

U.S. PATENT DOCUMENTS

| 3,123,077 | A |   | 3/1964  | Alcamo |
|---|---|---|---|---|
| 3,700,544 | A |   | 10/1972 | Matsui |
| 3,716,058 | A |   | 2/1973  | Tanner, Jr. |
| 3,720,055 | A |   | 3/1973  | DeMestral et al. |
| 3,833,972 | A |   | 9/1974  | Brumlik |
| 3,845,641 | A |   | 11/1974 | Waller |
| 3,981,051 | A |   | 9/1976  | Brumlik |
| 3,986,331 | A | * | 10/1976 | Brumlik ........................... 57/244 |
| 4,069,825 | A |   | 1/1978  | Akiyama |
| 4,548,202 | A |   | 10/1985 | Duncan |
| 4,880,585 | A |   | 11/1989 | Klimesch et al. |
| 4,900,605 | A |   | 2/1990  | Thorgersen et al. |
| 5,269,783 | A |   | 12/1993 | Sander |
| 5,269,809 | A |   | 12/1993 | Hayhurst et al. |
| 5,342,376 | A |   | 8/1994  | Ruff |
| 5,393,475 | A |   | 2/1995  | Murasaki et al. |
| 5,395,126 | A |   | 3/1995  | Tresslar |
| 5,425,747 | A |   | 6/1995  | Brotz |
| 5,584,859 | A |   | 12/1996 | Brotz |
| 5,931,855 | A |   | 8/1999  | Buncke |
| 5,964,783 | A |   | 10/1999 | Grafton et al. |
| 5,967,154 | A | * | 10/1999 | Anderson ....................... 132/321 |
| 6,018,840 | A | * | 2/2000  | Guay et al. .................... 15/207.2 |
| 6,162,537 | A |   | 12/2000 | Martin et al. |

(Continued)

FOREIGN PATENT DOCUMENTS

DE 1810800 6/1970
EP 0204931 B1 12/1986

(Continued)

OTHER PUBLICATIONS

Dattilo, P.P. Jr., et al., "Tissue Holding Performance of Knotless Absorbable Sutures", Society for Biomaterials 29th Annual Meeting Transactions (2003) p. 101.

(Continued)

*Primary Examiner* — Julian Woo
*Assistant Examiner* — Christopher L Templeton

(57) ABSTRACT

A suture including a shaft extending longitudinally along a length of the suture, and a plurality of barbs extending outwardly from said shaft. At least one of the barbs is non-symmetrical about a primary plane extending along the longitudinal length of the suture, and bisecting a distal tip of the barb and a center of the shaft.

3 Claims, 7 Drawing Sheets

(56) References Cited

U.S. PATENT DOCUMENTS

| | | |
|---|---|---|
| 6,241,747 B1 | 6/2001 | Ruff |
| 6,270,517 B1 | 8/2001 | Brotz |
| 6,581,367 B1 * | 6/2003 | Virag et al. .................. 59/92 |
| 6,599,310 B2 | 7/2003 | Leung et al. |
| 6,624,097 B2 | 9/2003 | Martin et al. |
| 6,776,789 B2 | 8/2004 | Bryant et al. |
| 6,848,152 B2 | 2/2005 | Genova et al. |
| 7,070,610 B2 | 7/2006 | Im et al. |
| 7,478,460 B2 | 1/2009 | Gallant et al. |
| 7,723,395 B2 | 5/2010 | Ringeisen et al. |
| 7,850,894 B2 | 12/2010 | Lindh, Sr. et al. |
| 7,913,365 B2 | 3/2011 | Genova et al. |
| 2001/0023020 A1 | 9/2001 | Martin et al. |
| 2003/0001407 A1 | 1/2003 | Hoshikawa et al. |
| 2003/0041426 A1 | 3/2003 | Genova et al. |
| 2003/0074023 A1 | 4/2003 | Kaplan et al. |
| 2003/0149447 A1 | 8/2003 | Morency et al. |
| 2004/0009028 A1 | 1/2004 | Gueret |
| 2004/0060409 A1 | 4/2004 | Lleung et al. |
| 2004/0060410 A1 | 4/2004 | Leung et al. |
| 2004/0088003 A1 | 5/2004 | Leung et al. |
| 2004/0093028 A1 | 5/2004 | Ruff |
| 2004/0138705 A1 | 7/2004 | Heino et al. |
| 2004/0193191 A1 | 9/2004 | Starksen et al. |
| 2005/0118388 A1 | 6/2005 | Kingsford |
| 2005/0203576 A1 | 9/2005 | Sulamanidze et al. |
| 2005/0240224 A1 | 10/2005 | Wu |
| 2005/0260398 A1 | 11/2005 | Owens |
| 2006/0079935 A1 | 4/2006 | Kolster |
| 2006/0135994 A1 | 6/2006 | Ruff et al. |
| 2006/0135995 A1 | 6/2006 | Ruff et al. |
| 2007/0005110 A1 | 1/2007 | Collier et al. |

FOREIGN PATENT DOCUMENTS

| | | |
|---|---|---|
| EP | 0464480 B1 | 1/1992 |
| EP | 0795336 B1 | 9/1997 |
| EP | 0831763 B1 | 10/2001 |
| EP | 1457214 A1 | 9/2004 |
| EP | 1075843 B1 | 2/2005 |
| EP | 1429664 B1 | 3/2007 |
| GB | 1091282 | 11/1967 |
| JP | 2003339849 | 12/2003 |
| WO | WO 96/06565 A1 | 3/1996 |
| WO | WO 99/01071 A1 | 1/1999 |
| WO | WO 99/49792 A1 | 10/1999 |
| WO | WO 00/16715 A1 | 3/2000 |
| WO | WO 03/017850 A2 | 3/2003 |
| WO | WO 03/044253 A1 | 5/2003 |
| WO | WO 03/083191 | 10/2003 |
| WO | WO 2004/030520 A2 | 4/2004 |
| WO | WO 2004/030704 A2 | 4/2004 |
| WO | WO 2004/030705 A | 4/2004 |
| WO | WO 2004/030705 A2 | 4/2004 |
| WO | WO 2006/005144 A1 | 1/2006 |
| WO | WO 2006/061868 A1 | 6/2006 |

OTHER PUBLICATIONS

Mckenzie, A.R., "An Experimental Multiple Barbed Suture for The Long Flexor Tendons of the Palm and Fingers", The Journal of Bone and Joint Surgery, (1967) vol. 49B, No. 3, pp. 440-447.

Schmid, A. et al., "The outspreading anchor cord". A material for anthroscopic suturing of a fresh anterior cruciate ligament rupture.

* cited by examiner

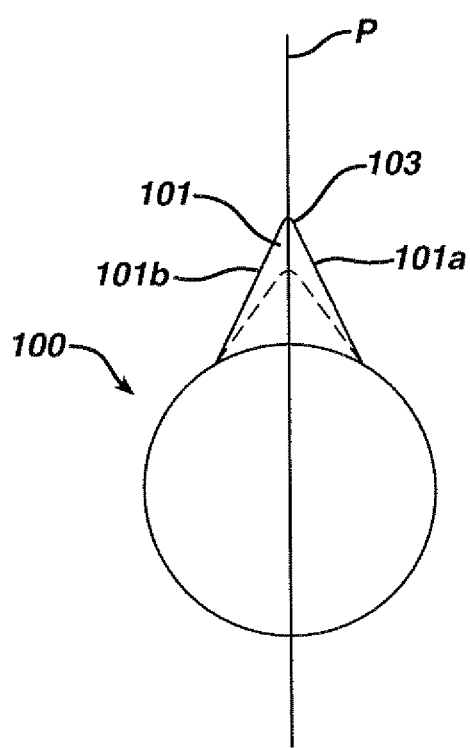
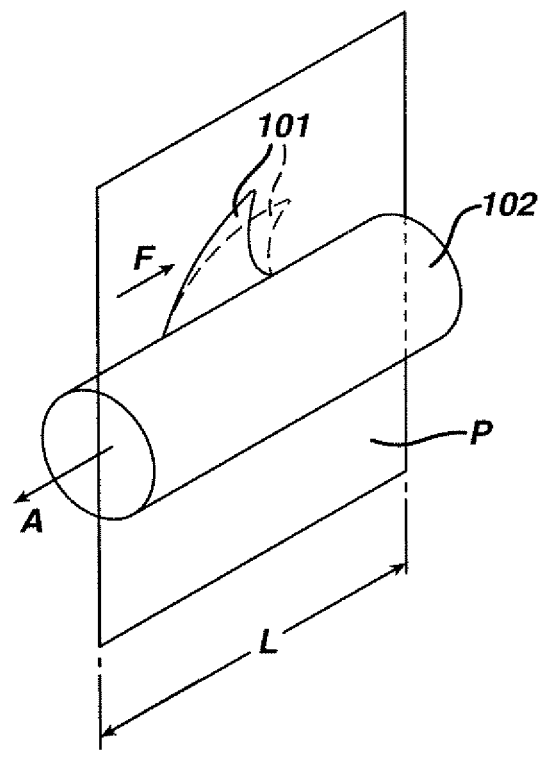
FIG. 1
FIG. 1a

BARBED SUTURE WITH NON-SYMMETRIC
BARBS

FIELD

The present invention relates generally to barbed sutures, and more particularly to barbed sutures having non-symmetrical barbs.

BACKGROUND

Many wound and surgical incisions are closed using surgical sutures or some other surgical closure device. Barbed sutures are well known and have recently been gaining attention for various medical applications. Typically, barbed sutures are constructed with a series of "barbs" or "protrusions" (used interchangeably herein) that extend outwardly from the suture, and function to increase the holding strength of the suture and/or eliminate the need for knot tying.

With any barbed suture, the tensile strength and holding strength of the suture are always of concern. The size and configuration of the barbs influence the holding strength, or the ability to grasp tissue and resist pull-out, but there are practical limitations on the ability to change their size and configuration, as this will also have an affect on insertion force, or the force required to draw the suture through tissue, and the overall stiffness of the suture.

Therefore, there remains a need to enhance barbed holding strength without significantly increasing the insertion force or stiffness of the suture.

SUMMARY OF THE INVENTION

The present invention provides a suture having a shaft extending longitudinally along a length of said suture, and a plurality of barbs extending outwardly from said shaft. At least one of the barbs is non-symmetrical about a primary plane extending along the longitudinal length of the suture, and bisecting a distal tip of the barb and a center of the shaft.

According to one embodiment, the at least one barb is geometrically non-symmetrical about said primary plane, and may further include a first portion on a first side of the primary plane and a second portion on a second side of the primary plane, where the first and second portions are made of the same material, and wherein the first portion has less mass than the second portion. In an alternate embodiment, the at least one barb includes a first portion on a first side of the primary plane and a second portion on a second side of the primary plane, where only the first portion has a recess therein.

In yet another embodiment, the at least one barb includes a first portion on a first side of the primary plane and a second portion on a second side of the primary plane, and the suture further includes at least one external element that is coupled to and extends between the first or second portion and the suture shaft. In yet another embodiment, the suture further includes at least a first set of barbs spaced apart longitudinally along the shaft, and at least one external element that is coupled to and extends between a first side of one of said first set of barbs to a second side of a second one of the first set of barbs.

According to another embodiment of the invention, the at least one barb is physically non-symmetrical about said primary plane. The non-symmetrical barb may include a first portion on a first side of the primary plane and a second portion on a second side of the primary plane, where the first portion is made of a first material and the second portion is made of a second material, or may include a first portion on a first side of the primary plane and a second portion on a second side of the primary plane, where the first portion is made of a different composition of materials than the second portion.

Also provided is a suture including a suture shaft having a plurality of barbs extending outwardly therefrom that, when the suture is not exposed to external forces, each of the plurality of barbs are non-symmetrical about a primary plane, and when the suture is being drawn through tissue by a first end thereof, at least a distal tip of the plurality of barbs moved out of the primary plane.

BRIEF DESCRIPTION OF THE DRAWINGS

FIGS. 1 and 1a illustrate an exemplary barbed suture having substantially symmetrical bars;

DETAILED DESCRIPTIONS

Figure 2:
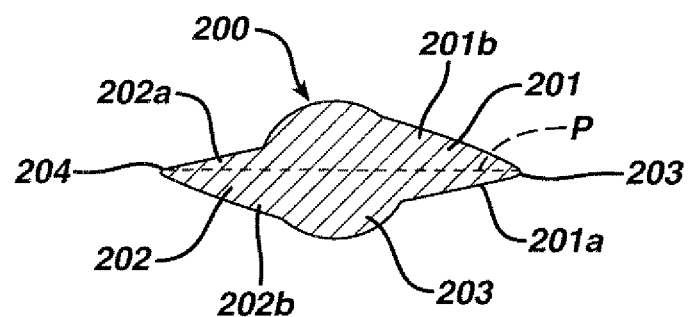
FIGS. 2 and 2a illustrate one embodiment of a barbed suture according to the present invention having non-symmetrical barbs.

Before explaining the present invention in detail, it should be noted that the invention is not limited in its application or use to the details of construction and arrangement of parts illustrated in the accompanying drawings and description. The invention as illustrated may be implemented or incorporated in other embodiments, variations and modifications, and may be practiced or carried out in various ways.

Referring once again to FIGS. 1 and 1a, these figures are exemplary illustrations of barbed sutures having a plurality of barbs or protrusions 101 that extend outwardly from the suture shaft 102, and that are substantially symmetrically formed around a plane P that includes the distal tip 103 of the barb, bisects the center of the suture shaft and also extends longitudinally along the length L of the suture shaft. For the purposes of this disclosure, such a plane will be referred to as a "primary plane." As further shown, for such symmetrically formed barbs, when an insertion force F is exerted on the barb during insertion of the suture in the direction illustrated by "A" in FIG. 1a, due to its symmetrical configuration, the force will be substantially equally and symmetrically distributed as among the portion of the barb 101a on one side of the primary plane and the portion of the barb 101b on the second side of the plane. Thus, to the extent the barb bends or collapses at all during insertion, it should remain substantially symmetric relative to the primary plane as illustrated by the dotted lines in FIGS. 1 and 1a.

In barbed sutures according to the present invention, however, the barbs are designed to be "non-symmetrical" about the primary plane so that the distal tip of the barb moves out of the primary plane during insertion and/or when under tension once inserted, as will be described further below. For the purposes of this disclosure, the term "non-symmetrical" is intended to include barbs that are geometrically non-symmetrical about the primary plane, and/or physically non-symmetrical (i.e., via use of different materials) about the primary plane, both of which are further described and illustrated below. For such sutures, when the suture reaches its resting place within tissue and the barbs tend to return towards their original state in a different plane, they are able to grasp undamaged tissue, or tissue that has not been damaged by being in the insertion path of the suture and/or barbs.

Figure 2A:
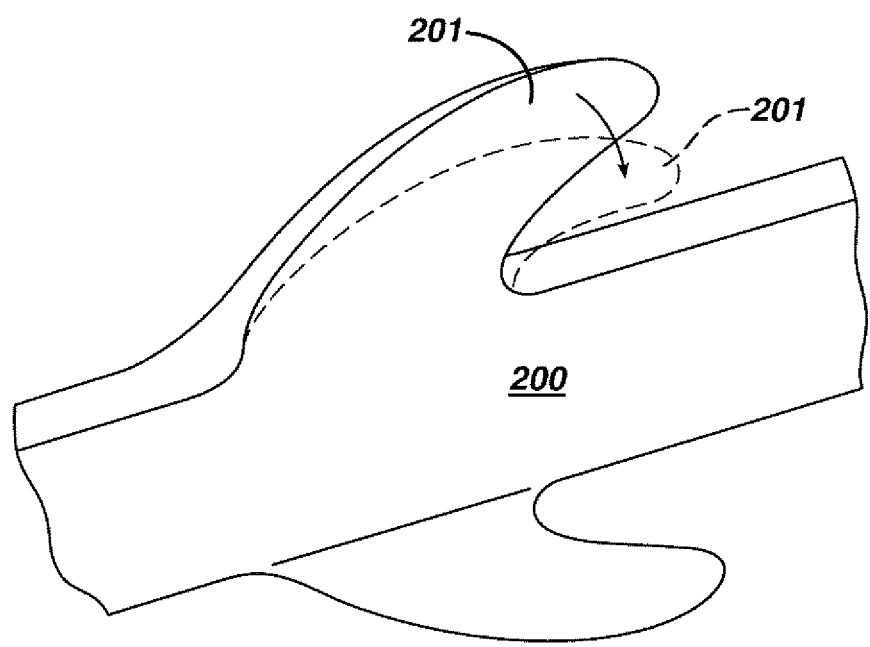

FIGS. 2-7 illustrate various embodiments of barbed sutures according to the present invention wherein the barbs rotate "out of plane" during insertion, meaning at least the distal tip of the barbs moves out of the primary plane at least during insertion. FIG. 2 is a cross section along the length of one embodiment of a barbed suture 200 having first and second barbs or projections 201, 202 extending outwardly from opposite sides of the suture shaft 203, where such barbs are not geometrically symmetrical about the primary plane P. Rather, each barb 201, 202 includes a first portion 201a, 202a on a first side of the primary plane P that is smaller in cross-section than a second portion 201b, 202b on the opposite side of the primary plane. Due to this non-symmetrical geometrical configuration, when forces F are place on the barbs during insertion of the suture into tissue, the first portions 201a, 202a will provide less resistance against this force than the second or opposite portions 201b, 202b, which will cause the barbs to somewhat fold or buckle away from the primary plane as shown by the dotted lines in FIG. 2a. Thus, at least the distal tip 203, 204 of the first and second barbs respectively will move out of the primary plane during insertion. Following insertion, the barbs will tend to return towards their original position in the primary plane, and into tissue not directly torn or damage during insertion. Further, when subsequently under tension when holding tissue together, the barbs will not only bend backward, but due to their non-symmetrical nature may similarly tend to move out of the primary plane.

Figure 3:
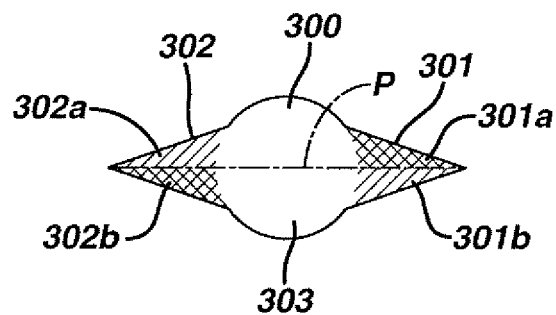
FIGS. 3-3b illustrate an alternate embodiment having barbs that are substantially geometrically symmetrical, but have nonsymmetrical composition of materials.

In an alternate embodiment shown in FIG. 3, the same objective is achieved by material selection for the barbs as opposed to creating a geometrically non-symmetrical barbs. The barbed suture 300 of FIG. 3 also includes a suture core or shaft 303 having first and second 301, 302 barbs projection outwardly from opposite sites. Each of the barbs 301, 302 is geometrically symmetrical about the primary plane P, but has a first portion 301a, 302a comprised substantially of a first material and a second portion 301b, 302b comprised substantially of a second material. The first material may be selected to be a substantially less stiff material, so that under the influence of insertion force F, the first portion provides less resistance, resulting in similar out of plane bending of the barbs as described above and as shown in FIG. 3a. Although geometrically symmetrical about the primary plane, such an embodiment is not physically symmetrical due to the differing materials, and is considered to be within the meaning of "non-symmetrical" as used herein. In exemplary embodiments, the first material may be polypropylene, polydioxanone, or copolymers of poly(glycolide-co-caprolactone), and the second material may be polyethylene, terephthalate or a polymer or copolymer of lactide and glycolide.

Figure 3A:
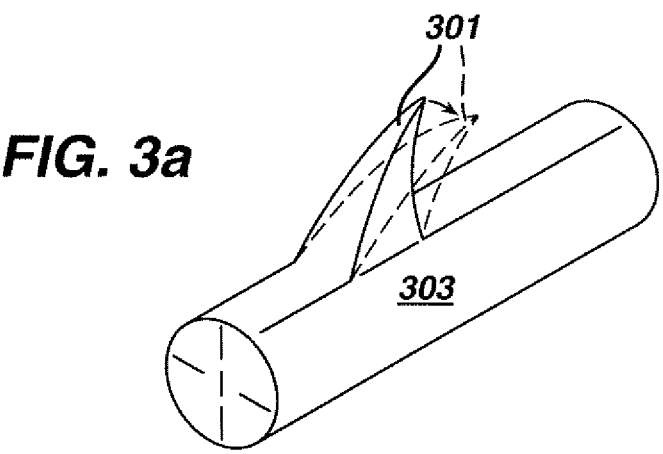
Figure 3B:
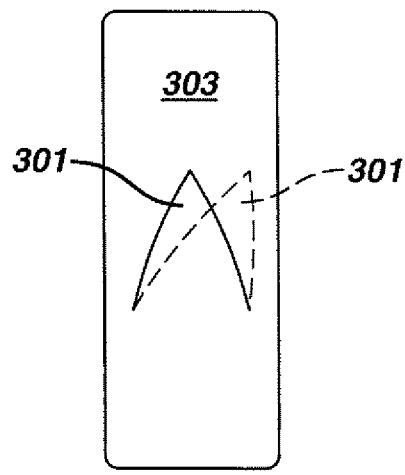

Although the embodiment of FIGS. 3-3b illustrate first and second barb portions each of an entirely different material, any varying combination of materials may also be suitable, so long as it results in different physical properties on each side of the primary plane. For example, only a portion of the second portion may be comprised of a second material. FIGS. 3a-3b illustrate such a barb in uncollapsed versus collapsed (dotted lines) states.

Figure 4:
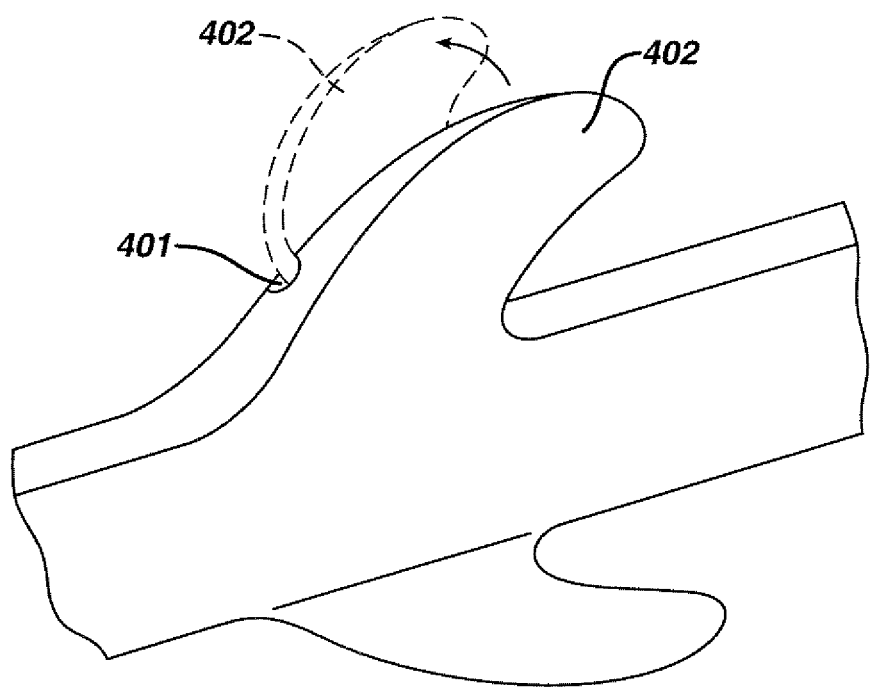
FIG. 4 illustrates yet another embodiment according to the present invention having non-symmetrical barbs.

In yet another embodiment, the barbs may be designed to have one or more recesses 401 in one side of the barbs 402, or non-symmetrical recesses on both sides (not shown), that will bias the barb to move out of plane during insertion as shown by the dotted line in FIG. 4.

Figure 5:
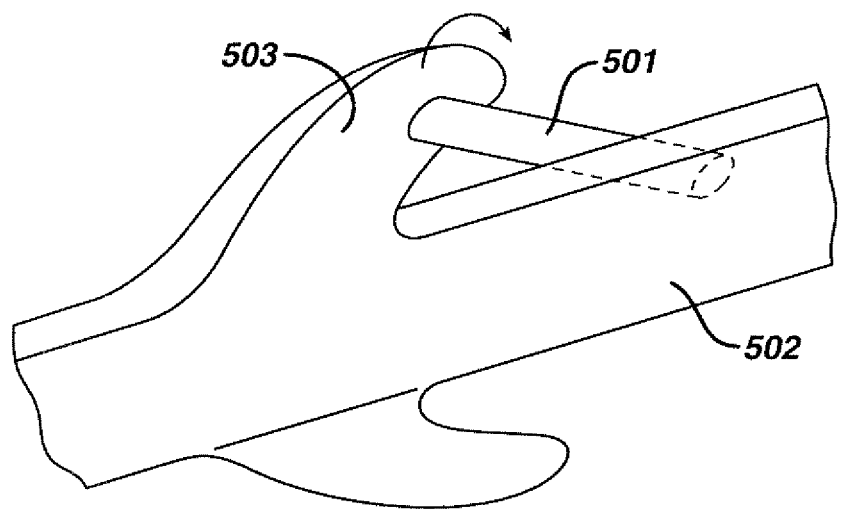
FIGS. 5-5b and 6-6b illustrate embodiments having additional bridges between the barbs and the suture shaft, or between successive barbs.
Figure 5A:
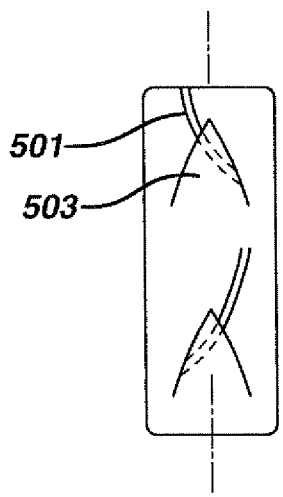
Figure 5B:
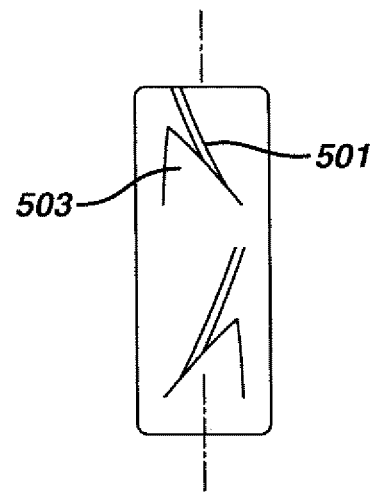
Figure 6:
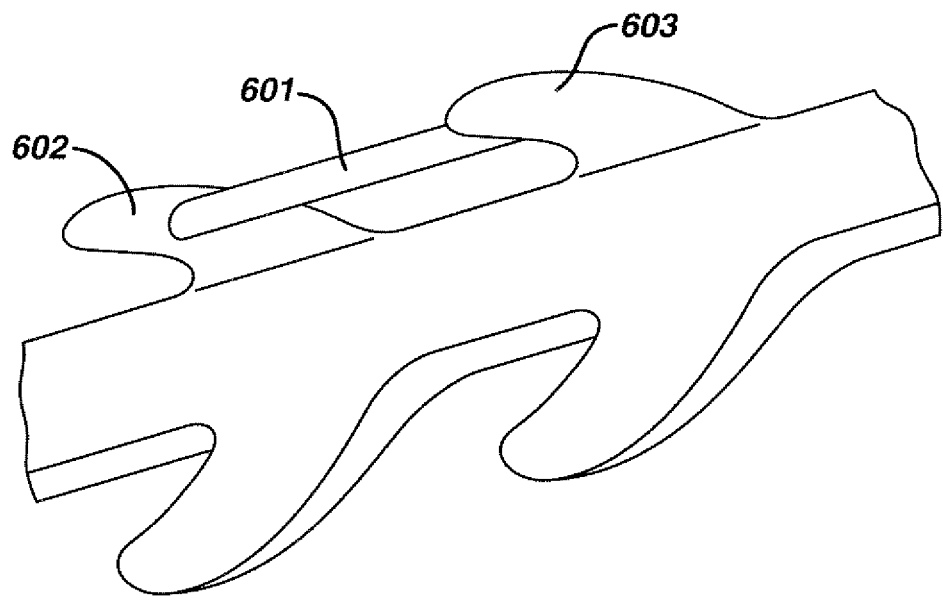
Figure 6A:
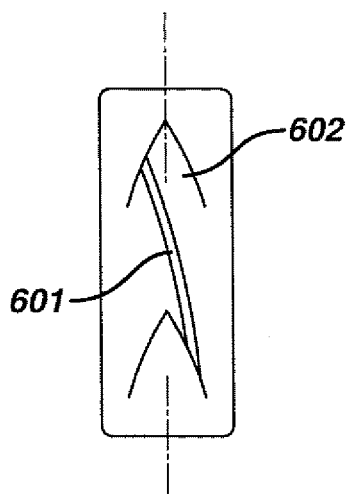
Figure 6B:
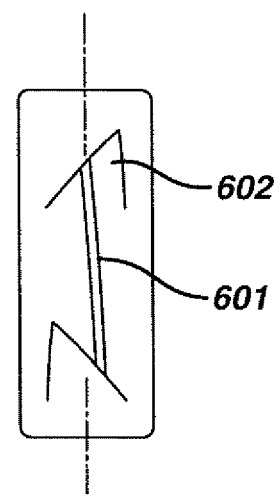

The embodiments of FIGS. 5 and 6 include external elements 501, 601 (that may or may not be comprised of the same material), that extend from the barbs 503 to the suture shaft 502 (FIG. 5), or from one barb 602 to an adjacent barb 603. In FIG. 5, the additional resistance on one side of the barb will promote non-symmetrical, out of plane movement during insertion as shown in FIGS. 5a and 6a (at rest) and FIGS. 5b and 6b (as collapsed during insertion).

Figure 7:
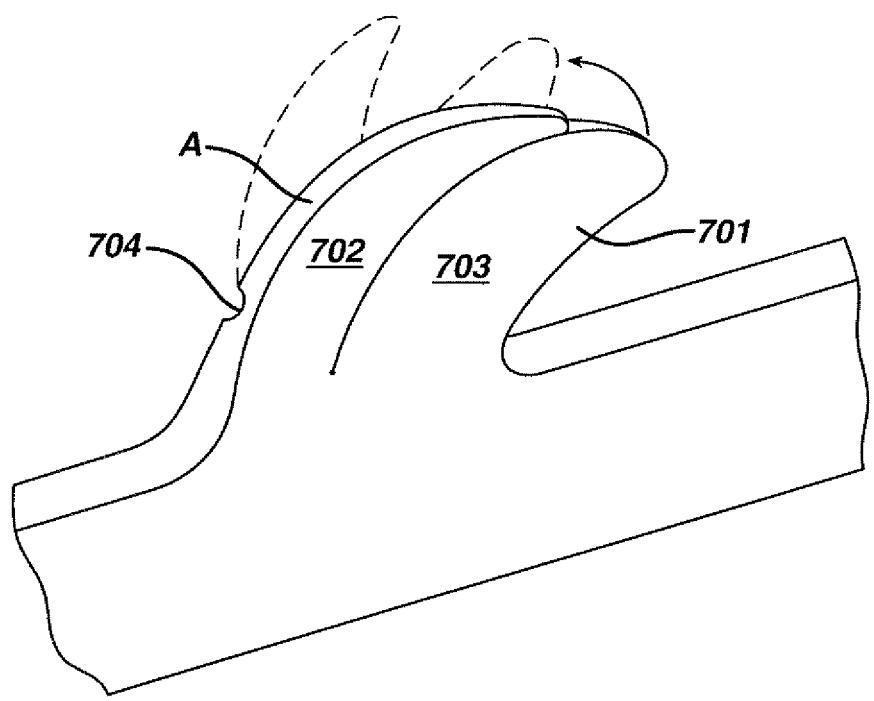
FIG. 7 illustrates yet another embodiment according to the present invention having split barbs.

Finally, the embodiment of FIG. 7 facilitates out of plane rotation of the barbs following engagement of the barbed suture with tissue following final placement of the suture. As shown, the barbed suture 700 includes barbs 701 that are bisected or split to include first and second barb portions 702, 703. The barb portions are aligned with and adjacent one another in the longitudinal direction of the suture shaft 704 with only the first barb portion 702 having a recess 704 therein such that only the first barb portion is biased to move out of the primary plane during insertion.

The sutures described herein may be made from any material suitable for surgical applications, and can be formed by any suitable process. Exemplary materials include both biodegradable polymers and non-biodegradable polymers. Suitable biodegradable polymers include, but are not limited to, poly(lactide), including L (−), D (+), meso and racemic lactide form, poly(glycolide), poly(dioxanone), poly(ϵ-caprolactone), poly(hydroxybutyrate), poly(□-hydroxybutyrate), poly(hydroxyvalerate), poly(tetramethylene carbonate), and poly(amino acids) and copolymers and terpolymers thereof. Other suitable materials include polyester amides, poly(phosphoresters)s, polyphosphazenes, poly(orthoester)s, poly(anhydride)s, anionic carbohydrate polymers, polysaccharides, poly(hydroxybutyric acid)s, polyacetals, poly(dl-lactide-co-glycolide)s, poly(l-lactide-co-glycolide)s, poly(alkylene diglycolate)s, poly(oxaester)s, poly(oxaamide)s, sulfonated aliphatic-aromatic copolyether esters, glyceride and dihydroxyacetone polymers. Suitable non-biodegradable polymers include, but are not limited to, polyetheretherketone (peek), polyetherketone, polymethylmethacrylate, polycarbonate, polyphenylenesulfide, polyphenylene, polyethylene terephthalate, Nylon, polyvinylfluoride, polyvinylidene fluoride, polypropylene, polyethylene, poly(vinylidene fluoride-co-hexafluoropropylene), poly(ethylene-co-hexafluoropropylene), poly(tetrafluoroethyelene-co-hexafluoropropylene), poly(tetrafluoroethyelene-co-ethylene), polyethyleneterephthalate, polyimides and polyetherimide. An exemplary process for forming such sutures include press forming and compound profile punching as described in detail in co-pending U.S. application Ser. No. 11/743,201, filed on May 2, 2007, which is incorporated herein by reference in its entirety.

The embodiments described herein have non-symmetrical barbs that bend or rotate out of plane during insertion or thereafter increase the holding strength of the suture, as the barbs are ultimately able to better grasp tissue that has not been damaged during insertion of the suture. Further, such barbed sutures can lower the insertion force as the barbs will bend or twist out of plane and lower the overall profile of the suture during insertion.

It is not intended that the invention described and illustrated herein be limited other than by the appended claims.

What is claimed is:

1. A surgical suture comprising:
   a suture shaft extending longitudinally along a length of said suture between a first end and a second end and comprised of a single monofilament, and having a plurality of barbs extending outwardly therefrom from a base to a distal tip, and having a wider base than the distal tip, wherein when the suture is not exposed to external forces, each of the plurality of barbs are non-symmetrical about a primary plane that extends along the length of the suture and bisects an entire length between the base and the distal tip for each of the plurality of barbs, and a center of said shaft, wherein each of the plurality of barbs has a first portion on a first side of the primary plane and a second portion on a second side of the primary plane, and wherein when the suture is being drawn through tissue by the first end thereof, at least one of the distal tips of the plurality of barbs moves out of the primary plane, wherein the suture shaft and plurality of barbs are integrally formed from a single, uniform, biocompatible material, and wherein the suture is configured for use as a surgical suture to approximate tissue.

2. The suture according to claim 1, wherein the plurality of barbs are geometrically non-symmetrical about said primary plane.

3. The suture according to claim 2, wherein the first and second portions are comprised of the same material, and wherein the first portion has less mass than the second portion.

* * * * *